United States Patent [19]

Watanabe et al.

[11] Patent Number: 4,966,918

[45] Date of Patent: Oct. 30, 1990

[54] DERIVATIVES OF CHRYOSPHANOL

[75] Inventors: Kyoichi A. Watanabe, Rye-Brook, N.Y.; Masao Koyama, Yokohama, Japan

[73] Assignee: Sloan-Kettering Institute for Cancer Research, New York, N.Y.

[21] Appl. No.: 302,836

[22] Filed: Jan. 27, 1989

[51] Int. Cl.$^5$ .................... A01N 33/10; C07C 50/18
[52] U.S. Cl. .................... 514/656; 514/676; 552/262; 552/266
[58] Field of Search ............ 260/380, 383, 384, 378; 514/676, 680, 656; 552/262, 269

[56]     References Cited
U.S. PATENT DOCUMENTS 4,215,062   7/1980   Mitscher .......................... 260/369

OTHER PUBLICATIONS

Venkataraman, *The Chemistry of Synthetic Dyes*, 1952, p. 831.
Barnett, *Anthracene and Anthraquinone*, 1921, pp. 174–175.

*Primary Examiner*—Richard L. Raymond
*Assistant Examiner*—Raymond Covington

*Attorney, Agent, or Firm*—John P. White

[57]    ABSTRACT

The present invention concerns compounds of the formula:

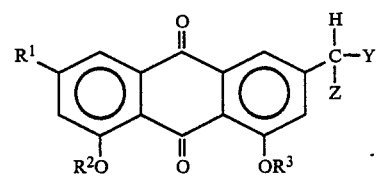

wherein
$R^1$ hydrogen, a hydroxyl group or a methoxy group;
$R^2$ is hydrogen or a methyl group;
$R^3$ is hydrogen or a methyl group;
Y is a halogen, a secondary amino group or a tertiary amino group; and
Z is hydrogen or a halogen.

The invention further concerns pharmaceutical compositions which comprises the above-identified compound or the acid salts thereof, and the use of the compound or compositions for treating a malignancy in a subject.

10 Claims, No Drawings

DERIVATIVES OF CHRYOSPHANOL,

The invention described herein was made in the course of work under Grant Nos. CA-08748 and CA-18856 from the National Cancer Institute, National Institutes of Health, U.S. Department of Health and Human Services. The U.S. Government has certain rights in this invention.

BACKGROUND OF THE INVENTION

Some of the information set forth herein has been published (see Masao Koyama, T. Ross Kelly and Kyoichi A. Watanabe, Novel Type of Potential Anticancer Agents Derived from Chrysophanol and Emodin). Some Structure-Activity Relationship Studies, Journal of Medicinal Chemistry, 1988, 31: 283–284, which was distributed by the publisher on Jan. 29, 1988.

Certain antitumor intercalating agents, e.g., ellipticine, m-AMSA and anthracycline antibiotics, have been the subject of structural modifications in order to gain better therapeutic potential. A number of analogs of ellipticine [LePeck, J. B., et al., Proc. Natl. Acad. Sci. U.S.A., 71: 5078 (1974); Guthrie, R. W., et al. J. Med. Chem., 18: 755 (1975)], m-AMSA [Denny, W.A., et al., J. Med. Chem., 25: 276 (1982)] and anthracycline antibiotics [Mosher, C. W., et al., J. Med. Chem., 25: 18 (1982); Seshadri, R., et al., J. Med. Chem., 26: 11 (1983); Li, L. H., et al., Cancer Res., 42: 999 (1982)] have been synthesized and screened for their anticancer activity. Unfortunately, however, preliminary screening data show that there is no straightforward structure-activity relationship between intercalating potency and anticancer activity.

These results seem to suggest that though intercalation may be a necessary condition, it may not be sufficient for such a drug to exert anticancer activity.

Recent studies on the mechanism of anticancer action of antibiotic CC1065 [Chidester, C. G., et al., J. Am. Chem. Soc., 103: 7629 (1981); Kanatomo, S., et al., Chem. pharm. Bull., 29: 229 (1981)] show that it binds to the minor groove of DNA by non-intercalative means and then slowly alkylates the amino group of adenine by opening the cyclopropane ring in the antibiotic molecule. With CC1065, covalent binding of the drug with DNA, therefore, seems to be important for its potent cytotoxic activity. Mere physical interaction between the drug and DNA may not be sufficient.

These considerations point to the development of intercalators with slow alkylating capability. Such intercalators will bind covalently and hopefully should eventually disrupt the DNA function.

The compounds of the present invention have both intercalating and alkylating functionalities, and as such are potential anticancer agents.

The compounds of this invention may also be useful as biochemical probes for biological reactions essential for DNA synthesis.

SUMMARY OF THE INVENTION

The present invention concerns compounds of the formula:

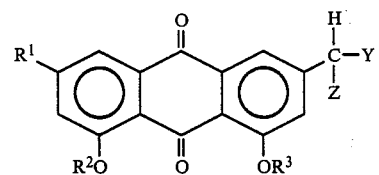

wherein
$R^1$ is hydrogen, a hydroxyl group or a methoxy group;
$R^2$ is hydrogen or a methyl group;
$R^3$ is hydrogen or a methyl group;
Y is a halogen, a secondary amino group or a tertiary amino group; and
Z is hydrogen or a halogen.

The invention further concerns pharmaceutical compositions which comprises the above-identified compound or the acid salts thereof, and the use of the compound or compositions for treating a malignancy in a subject.

DETAILED DESCRIPTION OF THE INVENTION

The present invention concerns compounds of formula (I):

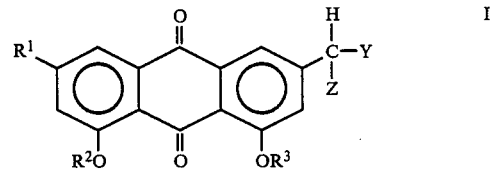

wherein
$R^1$ is hydrogen (H), a hydroxyl group (OH) or a methoxy group (OMe);
$R^2$ is hydrogen or a methyl group (Me);
$R^3$ is hydrogen or a methyl group;
Y is a halogen, a secondary amino group or a tertiary amino group; and
Z is hydrogen or a halogen.

When Y is a secondary amino group, e.g. [-NHalkyl], or a tertiary amino group, e.g. [-N(alkyl)$_2$], it is preferred that the alkyl groups be lower alkyl groups, e.g. groups having from one to about five carbon atoms. Particularly effective are methyl or ethyl groups. The lower alkyl groups may also have substituents on the carbon atoms for the hydrogens. The alkyl groups may be substituted with one or more hydroxyl group(s), for example 2-hydroxyethyl, or formed into organic acyl esters, such as acetyl, benzoyl or methanesulfonyl esters, i.e. the substituents are benzoxy, acetyloxy, or methylsulfonyloxy. Further, the alkyl groups may be substituted with halogen(s), such as chlorine and/or bromine to form groups such as a 2-chloroethyl or a 2-bromoethyl.

This invention also provides for pharmaceutical compositions for the treatment of a malignancy in a subject comprising the compound or a pharmaceutically acceptable acid salt thereof, and a pharmaceutically acceptable carrier. The amount of the composition being an amount effective to suppress the growth of the malignancy, preferably from 1-200 mg/kg of the body weight of the subject.

The invention further provides for a method of treating a subject having a malignancy which comprises administering to the subject an effective amount of the compound to suppress the growth of the malignancy. A subject may be any warm-blooded animal, preferably human. The malignancy is preferably a tumor or leukemia.

The following Experimental Detail Section and Examples are set forth to aid in an understanding of the invention. These sections are not intended to, and should not be construed to, limit in any way the invention set forth in the claims which follow thereafter.

EXPERIMENTAL DETAIL

The present invention provides a novel class of compounds, anthraquinones, which possess covalent bonding capability. Such compounds may intercalate into DNA and then bind covalently to DNA thereby exerting cytotoxic activity.

The starting materials for the compounds of the present invention are of the formula II:

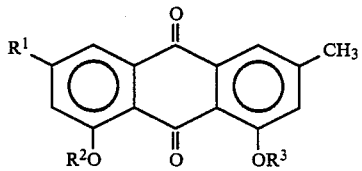

Typical examples contain the following combinations of $R^1$, $R^2$ and $R^3$.

|     | $R^1$ | $R^2$ and $R^3$ |             |
| --- | ----- | --------------- | ----------- |
| IIa | H     | H               | chrysophanol |
| IIb | OH    | H               | emodin      |
| IIc | H     | Me              |             |
| IId | OMe   | H               |             |
| IIe | OMe   | Me              |             |

Compounds IIc–IIe are known, and can be prepared readily from the natural product, chrysophanol or emodin (IIa or IIb), by the known procedures.

Compounds of formula II are treated with N-bromosuccinimide (NBS) or 1,3-dibromo-5,5-dimethylhydantoin (BMH) in an halogenated hydrocarbon, preferably carbon tetrachloride, in the presence of a peroxide, such as m-chloroperbenzoic acid or benzoyl peroxide to give the corresponding monobromides of the formula III as the major products and dibromides of formula IV as the minor products:

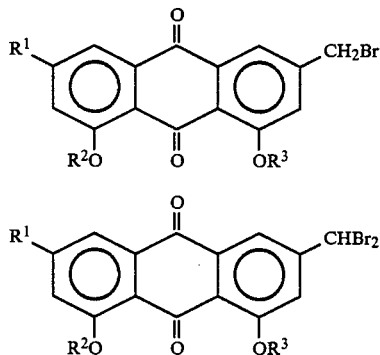

The reaction is carried out at a temperature range of from 25° C. to 100° C., preferably at the boiling temperature of the solvent (77° C. for carbon tetrachloride) in a period from one hour to three days. The molar ratio of the reactants, formula II to NBS or BMH, can be from 1:1 to 1:3, preferably 1:1.2. Upon completion of the reaction, insoluble materials are removed by filtration, the filtrate concentrated, and the residue recrystallized to give formula III compounds. From the mother liquor, formula IV compounds can be obtained after chromatography on a silica gel column.

The 1,8-dimethoxy derivatives IIIc, IIIe, IVc and IVe can be converted into the corresponding 1,8-dihydroxy derivatives IIIa, IIId, IVa and IVd, respectively, by treatment with hydrogen bromide in acetic acid.

Treatment of compounds of formula III with a primary or secondary amine of or without solvent affords the corresponding products with formula V:

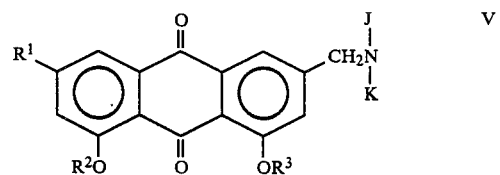

Some of the typical examples contain the following combinations of $R^1$, $R^2$, $R^3$, J and K.

| V  | $R^1$ | $R^2$ and $R^3$ | J          | K          |
| -- | ----- | --------------- | ---------- | ---------- |
| Va | H     | H               | Et         | Et         |
| Vb | H     | H               | CH2CH2OH   | CH2CH2OH   |
| Vc | H     | H               | Et         | H          |
| Vd | H     | H               | CH2CH2OH   | H          |
| Ve | OMe   | H               | Et         | Et         |
| Vf | OMe   | H               | CH2CH2OH   | CH2CH2OH   |
| Vg | OMe   | H               | Et         | H          |
| Vh | OMe   | H               | CH2CH2OH   | H          |
| Vi | H     | Me              | Et         | Et         |
| Vj | H     | Me              | CH2CH2OH   | CH2CH2OH   |
| Vk | H     | Me              | Et         | H          |
| Vl | H     | Me              | CH2CH2OH   | H          |
| Vm | OMe   | Me              | Et         | Et         |
| Vn | OMe   | Me              | CH2CH2OH   | CH2CH2OH   |
| Vo | OMe   | Me              | Et         | H          |
| Vp | OMe   | Me              | CH2CH2OH   | H          |

The 1,8-dimethoxy derivatives of formula V (Vi–Vp) can be converted into their corresponding 1,8-dihydroxyanthraquinones of formula V (va–Vh) by treatment with hydrogen bromide in acetic acid.

The 2-hydroxyethylamino derivatives (Vb, Vd, Vf, Vh, Vj, Vl, Vn and Vp) can be further converted into their corresponding 2-chloroethyl derivatives (Vq–Vx) by treatment with a conventional chlorinating agent, such as thionyl chloride, sulfonyl chloride, phosphorus oxychloride or carbon tetrachloride and triphenylphosphine.

| V  | $R^1$ | $R^2$ and $R^3$ | J         | K         |
| -- | ----- | --------------- | --------- | --------- |
| Vq | H     | H               | CH2CH2Cl  | CH2CH2Cl  |
| Vr | H     | H               | CH2CH2Cl  | H         |
| Vs | OMe   | H               | CH2CH2Cl  | CH2CH2Cl  |
| Vt | OMe   | H               | CH2CH2Cl  | H         |
| Vu | H     | Me              | CH2CH2Cl  | CH2CH2Cl  |
| Vv | H     | Me              | CH2CH2Cl  | H         |
| Vw | OMe   | Me              | CH2CH2Cl  | CH2CH2Cl  |
| Vx | OMe   | Me              | CH2CH2Cl  | H         |

The reaction is carried out at a temperature range of from 0° C. to 100° C., preferably at room temperature, in a period from half an hour to eight hours, in a solvent such as N,N-dimethylformamide, N,N-dimethylacetamide, diethyl ether or tetrahydrofuran, preferably in N,N-dimethylformamide.

In a similar manner, the corresponding 2-bromoethyl derivatives can be obtained by bromination of the 2-hydroxyethyl intermediates with thionyl bromide, phosphorus oxybromide or carbon tetrabromide and triphenylphosphine in N,N-dimethylformamide.

Acylation of the 2-hydroxyethyl intermediates with acid anhydride, such as acetic anhydride, benzoic anhydride or methanesulfonic anhydride, or with acyl chloride, such as acetyl chloride, benzoyl chloride or methanesulfonyl chloride, in pyridine or in a mixture of chloroform and p-dimethylaminopyridine or methylenechloride and p-dimethylaminopyridine, affords the corresponding acyl derivatives.

The following examples are illustrative of the process and products of the present invention, but are not to be construed as limiting.

EXAMPLE 1

To a hot solution of 1,8-dimethoxy-3-methyl-9,10-anthraquinone (4.5 g, 16 mM) and 1,3-dibromo-5,5-dimethylhydantoin (2.75 g, 19.2 mM) in carbon tetrachloride (500 mL) is added benzoyl peroxide (0.7 g), and the mixture is heated under reflux for 5 hours. The mixture is allowed to cool to room temperature. Insoluble hydantoin is removed by filtration, the filtrate is concentrated to dryness, and the residue recrystallized twice from ethyl acetate to give 3-bromomethyl-1,8-dimethoxy-9,10-anthraquinone (3.3 g, 57%), mp 176–178° C. 1H NMR (CDCl$_3$) δ: 4.01 (3H, s, OMe), 4.03 (3H, s, OMe), 4.52 (2H, s, CH2Br), 7.26–7.84 (5H, m, aromatic H). Analyses (C$_{17}$H$_{13}$BrO$_4$). Calculated: C, 56.53; H, 3.63; Br, 22.12. Found: C, 56.48; H, 3.67; Br, 21.93.

The mother liquors of recrystallization of above are concentrated, and the residue chromatographed on a silica gel column using a mixture of benzene and ethyl acetate. 3-Dibromomethyl-1,8-dimethoxy-9,10-anthraquinone (0.4B g) is eluted from the column followed by 3-bromomethyl-1,8-dimethoxy-9,10-anthraquinone (0.33 g). The former has the following characteristics: mp 207°–210° C., 1H NMR (CDCl$_3$) δ: 4.01 (3H, s, OMe), 4.07 (3H, s, OMe), 6.67 (1H, s, CHBr2), 7.26–7.92 (5H, m, aromatic H). Analyses (C$_{17}$H$_{18}$Br$_2$O$_4$). Calculated: C, 46.40; H, 2.75; Br, 36.31. Found: C, 46.63; H, 2.87; Br, 36.23.

The following the same procedure but using the corresponding anthraquinones as the starting materials, the following 3-bromomethyl- and 3,3-dibromomethyl-9,10-anthraquinones are prepared:
3-Bromomethyl-1,6,8-trimethoxy-9,10-anthraquinone,
3-Dibromomethyl-1,6,8-trimethoxy-9,10-anthraquinone,
3-Bromomethyl-1,8-dihydroxy-9,10-anthraquinone,
3-Bromomethyl-1,8-dihydroxy-9,10-anthraquinone,
3-Bromomethyl-1,6,8-trihydroxy-9,10-anthraquinone,
3-Dibromomethyl-1,6,8-trihydroxy-9,10-anthraquinone,
3-Bromomethyl-1,8-dihydroxy-6-methoxy-9,10-anthraquinone,
3-Dibromomethyl-1,8-dihydroxy-6-methoxy-9,10-anthraquinone.

By following the same procedure, but using N-bromosuccinimide instead of 3,3-dibromo-5,5-dimethylhydantoin, the same products above are prepared from their corresponding 3-methyl-9,10,-anthraquinone starting materials.

EXAMPLE 2

A mixture of 3-bromomethyl-1,8-dimethoxy-9,10-anthraquinone (1.05 g), 30% hydrogen bromide in acetic acid (5 mL) and acetic acid (50 mL) is heated at 100° C. for 5 hours. After cooling the mixture, 3-bromomethyl-1,8-dihydroxy-9,10-anthraquinone is collected by filtration, washed with acetic acid, and then air-dried to give 879 mg (91%) of the product, mp 220–222° C. 1H NMR (CDCl$_3$) δ: 4.47 (2H, s, CH2Br), 7.27–7.91 (5H, m, aromatic H), 12.02 (1H, s, OH), 12.05 (1H, s, OH). Analyses (C$_{15}$H$_9$BrO$_4$). Calculated: C, 54.08; H, 2.71; Br, 23.99. Found: C, 54.00; H, 2.92; Br, 24.16.

By following the same procedure but using the corresponding 1,8-dimethoxy-9,10-anthraquinones, the following compounds are prepared:
3-Dibromomethyl-1,8-dihydroxy-9,10-anthraquinone,
3-Bromomethyl-1,8-dihydroxy-6-methoxy-9,10-anthraquinone, 3-Dibromomethyl-1,8-dihydroxy-6-methoxy-9,10-anthraquinone,

EXAMPLE 3

A mixture of 3-bromomethyl-1,8-dihydroxy-9,10-anthraquinone (456 mg) and bis(2-hydroxyethyl)amine (600 mg) in N,N-dimethylformamide (20 mL) is stirred for 2 hours, and then partitioned between chloroform (100 mL) and water (100 mL). The organic layer is separated, washed with water (50 mL×3), dried over sodium sulfate, and then concentrated to dryness. The residue is chromatographed on a silica gel column using chloroform-methanol (15:1 v/v) as the eluent. Upon concentration of the major fraction, 3-[N,N-bis(2-hydroxyethyl)amino]methyl-1,8-dihydroxy-9,10-anthraquinone is obtained as a solid: 1H NMR (CDCl$_3$) δ: 2.77 (4H, t, NCH2CH2O), 3.78 (4H, t, NCH2CH2O), 3.78 (2H, s, CH2N=), 7.21–7.79 (5H, m, aromatic H), 11.95 (1H, s, OH), 12.00 (1H, s, OH).

The solid is dissolved in 1N hydrochloric acid, and the solvent is removed in vacuo. The crystalline hydrochloride salt (495 mg, 91%) is triturated with methanol (5 mL), mp 204°–207° C. (decomposition). Analyses (C$_{19}$H$_{19}$.HCl). Calculated: C, 57.95; H, 5.12; N, 3.56. Found: C, 58.00; H, 5.26; N, 3.37.

By following the same procedure but using the corresponding 3-bromomethyl-9,10-anthraquinones, the following compounds and their hydrochloric acid salts are prepared:
3-[N,N-Diethylamino)methyl-1,8-dihydroxy-9,10-anthraquinone,
3-(N-Ethylamino)methyl-1,8-dihydroxy-9,10-anthraquinone,
3-[N-(2-Hydroxyethyl)amino]methyl-1,8-dihydroxy-9,10-anthraquinone,
3-(N,N-Diethylamino)methyl-1,8-dihydroxy-6-methoxy-9,10-anthraquinone,
3-[N,N-Bis(2-hydroxyethyl)amino]methyl-1,8-dihydroxy-6-methoxy-9,10-anthraquinone,
3-(N-Ethylamino)methyl-1,8-dihydroxy-6-methoxy-9,10-anthraquinone,
3-[N-(2-Hydroxyethyl)amino]methyl-1,8-dihydroxy-6-methoxy-9,10-anthraquinone,
3-(N,N-Diethylamino)methyl-1,8-dimethoxy-9,10-anthraquinone,
3-[N,N-Bis(2-hydroxyethyl)amino]methyl-1,8-dimethoxy-9,10-anthraquinone, 3-(N-Ethylamino)methyl-1,8-dimethoxy-9,10-anthraquinone, 3-[N-(2-Hydroxyethyl)amino]methyl-1,8-dimethoxy-9,10-anthraquinone, 3-(N,N-Diethylamino)methyl-1,6,8-trimethoxy-9,10-anthraquinone, 3-[N,N-Bis(2-hydroxyethyl)amino]methyl-1,6,8-trimethoxy-9,10-anthraquinone, 3-(N-Ethylamino)methyl-1,6,8-trimethoxy-9,10-anthraquinone, 3-[N-2-Hydroxyethyl)amino]methyl-1,6,8-trimethoxy-9,10-anthraquinone.

EXAMPLE 4

To a solution of 3-[N,N-bis(2-hydroxyethyl)amino]methyl-1,8-dihydroxy-9,10-anthraquinone (162 mg) in dry N,N-dimethylformamide (5 mL) is added thionyl chloride (0.2 mL). After 2 hours at room temperature, the mixture is concentrated in vacuo to dryness, and the residue is triturated well with methanol (3 mL). 3-[N,N-Bis(2-chloroethyl)amino]methyl-1,8-dihydroxy-9, 10-anthraquinone that is crystallized is collected by filtration, 172 mg (96%), mp 211°–214° C. (decomposition). $^1$H NMR (CDCl$_3$) δ: 3.48 (4H, t, NCH$_2$CH$_2$Cl), 3.85 (4H, t, NCH$_2$CH$_2$Cl), 4.34 (2H, d, CH$_2$N=), 7.32–7.95 (5H, m, aromatic H). Analyses (C$_{19}$H$_{17}$Cl$_2$NO$_4$.HCl). Calculated: C, 52.98; H, 4.21; Cl, 24.24; N, 3.25. Found: C, 52.79; H, 4.32; Cl, 24.41; N, 3.36.

By following the same procedure but using the corresponding (2-hydroxyethyl)amino derivatives, the following compounds are prepared:

3-[N-(2-Chloroethyl)amino]methyl-1,8-dihydroxy-9,10-anthraquinone,

3-[N,N-Bis(2-chloroethyl)amino]methyl-1,8-dihydroxy-6-methoxy-9,10-anthraquinone, 3-[N-(2-Chloroethyl)amino]methyl-1,8-dihydroxy-6-methoxy-9,10-anthraquinone, 3-[N,N-Bis(2-chloroethyl)amino]methyl-1,8-dimethoxy-9,10-anthraquinone, 3-[N-(2-Chloroethyl)amino]methyl-1,8-dimethoxy-9,10-anthraquinone, 3-[N,N-Bis(2-chloroethyl)amino]methyl-1,6,8-trimethoxy-9,10-anthraquinone, 3-[N-(2-Chloroethyl)amino]methyl-1,6,8-trimethoxy-9,10-anthraquinone.

EXPERIMENTAL DISCUSSION

Table I lists typical results supporting the use of the present compounds as anti-cancer agents in the treatment of subjects.

TABLE I

Inhibitory activity of some 9,10-anthraquinone derivatives.

| Compounds | melting point (°C.) | ID$_{50}$ (μg/mL) | ID$_{50}$ (μM) |
|---|---|---|---|
| IIa | 194–195 | >100 | >390 |
| IIb | 256–257 | >100 | >335 |
| Va (HCl) | 235–238 (dec) | 0.99 | 2.8 |
| Vb (HCl) | 204–207 (dec) | 2.33 | 5.9 |
| Vc (HCl) | >275 | 0.26 | 0.77 |
| Vd (HCl) | 255–261 (dec) | 0.066 | 0.16 |
| Ve (HBr) | 240–241 (dec) | 0.51 | 1.16 |
| Vf (HCl) | 225–227 (dec) | 5.80 | 13.7 |
| Vg (HBr) | >275 | 0.18 | 0.44 |
| Vh (HCl) | 259–260 (dec) | 0.072 | 0.19 |
| Vi (HCl) | 154–158 | 52.3 | 128.3 |
| Vj (HCl) | 202–205 (dec) | >21 | >49.8 |
| Vk (HCl) | 254–255 (dec) | 1.30 | 3.59 |
| Vl (HCl) | 251–252 (dec) | 53.7 | 142.0 |
| Vm (HCl) | 222–223 (dec) | 2.90 | 6.91 |
| Vn (HCl) | 226–227 (dec) | 12.5 | 27.7 |

TABLE I-continued

Inhibitory activity of some 9,10-anthraquinone derivatives.

| Compounds | melting point (°C.) | ID$_{50}$ (μg/mL) | ID$_{50}$ (μM) |
|---|---|---|---|
| Vo (HCl) | 267–269 (dec) | 1.44 | 3.67 |
| Vp (HCl) | 252–253 (dec) | 5.10 | 12.5 |
| Vq (HCl) | 211–214 (dec) | 0.058 | 0.13 |
| Vr (HCl) | 255–261 (dec) | 2.37 | 7.11 |
| Vs (HCl) | 203–206 (dec) | 0.010 | 0.023 |
| Vu (HCl) | 208–209 (dec) | 5.73 | 12.5 |
| Vw (HCl) | 200–201 (dec) | 1.30 | 2.66 |

The starting materials, chrysophanol and emodin (IIa and IIb), are capable of intercalating into DNA but do not possess covalent bond forming capability, and exhibit little anticancer activity. The 1,8-dimethoxy intermediates (Vu-Vx), that bear alkylating potential but are incapable of intercalating into DNA due to the presence of bulky methoxy groups, are active to a small extent against mouse leukemia L1210 cells. Those compounds that are capable of intercalating into DNA and bind covalently to the DNA after intercalation (Vq-Vt) do exhibit extremely potent activity against L1210 cells.

Table II lists additional results supporting the anticancer use of the present invention.

TABLE II

Antileukemic activity of chrysophanol derivatives bearing alkylating potential.

| J and K | R$^1$ | R$^2$ | R$^3$ | L1210: ID$_{50}$, μM |
|---|---|---|---|---|
| Et | H | Me | Me | 128.3 |
| Et | H | H (or Me) | Me (or H) | 11.9 |
| Et | H | H | H | 2.75 |
| CH$_2$CH$_2$OH | H | Me | Me | >50 |
| CH$_2$CH$_2$OH | H | H (or Me) | Me (or H) | 23.4 |
| CH$_2$CH$_2$OH | H | H | H | 5.92 |
| CH$_2$CH$_2$Cl | H | Me | Me | 12.5 |
| CH$_2$CH$_2$Cl | H | H (or Me) | Me (or H) | 1.40 |
| CH$_2$CH$_2$Cl | H | H | H | 0.13 |
| Et | OMe | Me | Me | 6.91 |
| Et | OMe | H | H | 1.16 |
| CH$_2$CH$_2$OH | OMe | Me | Me | >27.6 |
| CH$_2$CH$_2$OH | OMe | H | H | 13.7 |
| CH$_2$CH$_2$Cl | OMe | Me | Me | 2.66 |
| CH$_2$CH$_2$Cl | OMe | H (or Me) | Me (or H) | 1.75 |
| CH$_2$CH$_2$Cl | OMe | H | H | 0.023 |

3-[N,N-Bis(2-chloroethyl)amino]methyl-1,8-dihydroxy-9,10-anthraquinone (Vq) is extremely potent against mouse leukemia L1210 made resistant to Cisplatin. At the dosage of 100 mg/kg/day×5 (ip), mice inoculated with Cisplatin resistant leukemia L1210/Cisplatin are cured.

The process of treating tumors according to this invention comprises administering to a subject having an abnormal proportion of leukocytes or other evidence of a malignancy, a therapeutic nontoxic amount of a compound of the invention such as 3-[N,N-bis(2chloroethyl)amino]methyl-1,8-dihydroxy-9,10-anthraquinone, as such or in the form of a pharmaceutically acceptable salt thereof. The invention also provides a pharmaceutical composition in dosage unit form comprising from 1 to 200 mg/kg of a compound of the invention, per dosage unit, together with pharmaceutically acceptable nontoxic inert carrier or diluent thereof as described above. A subject may be any warm-blooded animal and is preferably human.

What is claimed is:

1. A compound having the structure:

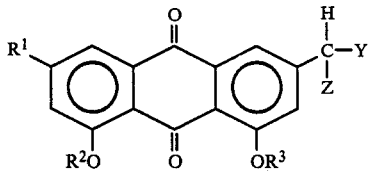

wherein
- R[1] is hydrogen, a hydroxy group or a methoxy group;
- R[2] is hydrogen or a methyl group;
- R[3] is hydrogen or a methyl group;
- Y is a halogen, a secondary amino group (NHalkyl) or a tertiary amino group (N(alkyl)$_2$); and
- Z is hydrogen or a halogen.

2. A compound of claim 1 wherein the halogen is chlorine or bromine.

3. A compound of claim 1, wherein the secondary amino group comprises a lower alkyl group or a substituted lower alkyl group where each substituent is a halogen or a hydroxy, benzoxy, or acetyloxy group.

4. A compound of claim 1, wherein the tertiary amino group comprises two lower alkyl groups or substituted lower alkyl groups where each substituent is a halogen or a hydroxy, benzoxy, or acetyloxy group and where the lower alkyl groups or the substituted lower alkyl groups are the same or different.

5. A compound of claim 1 selected from the group consisting of:
- 3-(N,N-Diethylamino)methyl-1,8-dihydroxy-9,10-anthraquinone;
- 3-(N,Ethylamino)methyl-1,8-dihydroxy-9,10-anthraquinone;
- 3-[N,N-Bis(2-hydroxyethyl)amino]methyl-1,8-dihydroxy-9,10-anthraquinone;
- 3-[N-(2-Hydroxyethyl)amino]methyl-1,8-dihydroxy-9,10-anthraquinone;
- 3-(N,N-Diethylamino)methyl-1,8-dihydroxy-6-methoxy-9,10-anthraquinone;
- 3-(N,Ethylamino)methyl-1,8-dihydroxy-6-methoxy-9,10-anthraquinone;
- 3-[N,N-Bis(2-hydroxyethyl)amino]methyl-1,8-dihydroxy-6-methoxy-9,10-anthraquinone;
- 3-[N-(2-Hydroxyethyl)amino]methyl-1,8-dihydroxy-6-methoxy-9,10-anthraquinone;
- 3-(N,N-Diethylamino)methyl-1,8-dimethoxy-9,10-anthraquinone;
- 3-(N,Ethylamino)methyl-1,8-dimethoxy-9,10-anthraquinone;
- 3-[N,N-Bis(2-hydroxyethyl)amino]methyl-1,8-dimethoxy-9,10-anthraquinone;
- 3-[N-(2-Hydroxyethyl)amino]methyl-1,8-dimethoxy-9,10-anthraquinone;
- 3-[N,N-Diethylamino)methyl-1,6,8-trimethoxy-9,10-anthraquinone;
- 3-(N,Ethylamino)methyl-1,6,8-trimethoxy-9,10-anthraquinone; and
- 3-[N,N-Bis(2-hydroxyethyl)amino]methyl-1,6,8-trimethoxy-9,10-anthraquinone.

6. A compound of claim 1 selected from the group consisting of:
- 3-[N,N-Bis(2-chloroethyl)amino]methyl-1,8-dihydroxy-9,10-anthraquinone;
- 3-[N-(2-Chloroethyl)amino]methyl-1,8-dihydroxy-9,10-anthraquinone;
- 3-[N,N-Bis(2-chloroethyl)amino]methyl-1,8-dihydroxy-6-methoxy-9,10-anthraquinone;
- 3-[N-(2-Chloroethyl)amino]methyl-1,8-dihydroxy-6-methoxy-9,10-anthraquinone;
- 3-[N,N-Bis(2-chloroethyl)amino]methyl-1,8-dimethoxy-9,10-anthraquinone;
- 3-[N-(2-Chloroethyl)amino]methyl-1,8-dimethoxy-9,10-anthraquinone;
- 3-[N,N-Bis(2-chloroethyl)amino]methyl-1,6,8-trimethoxy-9,10-anthraquinone; and
- 3-[N-(2-Chloroethyl)amino]methyl-1,6,8-trimethoxy-9,10-anthraquinone.

7. A pharmaceutical composition for the treatment of a malignancy in a subject comprising the compound of claim 1 or a pharmaceutically acceptable acid salt thereof and a pharmaceutically acceptable carrier, the amount of the compound or salt being 1 to 200 mg/kg of body weight of the subject.

8. A method of treating a subject having a malignancy which comprises administering to the subject an effective amount of the compound of claim 1 to suppress growth of the malignancy.

9. A method of claim 8, wherein the malignancy is leukemia.

10. A method of claim 8, wherein the malignancy is a tumor.